(12) United States Patent
Osipow et al.

(10) Patent No.: US 6,214,318 B1
(45) Date of Patent: Apr. 10, 2001

(54) AEROSOL OINTMENT COMPOSITIONS FOR TOPICAL USE

(75) Inventors: Lloyd I. Osipow, Boynton Beach, FL (US); Dorothea C. Marra, Summit, NJ (US); J. George Spitzer, Palm Beach, FL (US)

(73) Assignee: OMS Holdings LLC, New York, NY (US)

( * ) Notice: Subject to any disclaimer, the term of this patent is extended or adjusted under 35 U.S.C. 154(b) by 0 days.

(21) Appl. No.: 09/281,162

(22) Filed: Mar. 30, 1999

Related U.S. Application Data

(63) Continuation-in-part of application No. 09/174,858, filed on Oct. 19, 1998, now abandoned, which is a continuation-in-part of application No. 09/075,067, filed on May 8, 1998, now abandoned, which is a continuation-in-part of application No. 08/947,530, filed on Oct. 2, 1997, now abandoned.

(51) Int. Cl.[7] .............................. A61K 9/12; A61K 9/107
(52) U.S. Cl. ................... 424/45; 424/78.05; 424/78.07; 514/63; 514/944; 514/945; 514/937; 514/938
(58) Field of Search .................... 424/45, 78.05, 424/78.07; 514/944, 945, 937, 938, 63

(56) References Cited

U.S. PATENT DOCUMENTS

| | | |
|---|---|---|
| 3,859,432 | 1/1975 | Dinerstein . |
| 3,970,584 | 7/1976 | Hart et al. . |
| 4,331,653 | 5/1982 | Brown et al. . |
| 4,422,887 | 12/1983 | Spitzer et al. . |
| 4,439,343 | 3/1984 | Albanese . |
| 4,716,032 | 12/1987 | Westfall et al. . |
| 4,981,677 | 1/1991 | Thau . |
| 5,002,680 | 3/1991 | Schmidt et al. . |
| 5,098,693 | 3/1992 | Faas, Jr. et al. . |
| 5,116,618 | 5/1992 | Hagarty . |
| 5,143,717 | 9/1992 | Davis . |
| 5,145,604 | 9/1992 | Neumiller . |
| 5,209,921 | 5/1993 | Brobyn et al. . |
| 5,302,376 | 4/1994 | Forestier et al. . |
| 5,352,437 | 10/1994 | Nakagawa et al. . |
| 5,397,564 | 3/1995 | Seki et al. . |
| 5,490,980 | * 2/1996 | Richardson et al. . |
| 5,496,538 | 3/1996 | Zimmerman et al. . |
| 5,518,712 | 5/1996 | Stewart . |
| 5,618,515 | 4/1997 | Singh et al. . |
| 5,621,012 | 4/1997 | Schönrock et al. . |
| 5,635,165 | 6/1997 | Panitch . |
| 5,679,360 | 10/1997 | de Lacharriere et al. . |
| 5,716,609 | 2/1998 | Jain et al. . |
| 5,718,916 | 2/1998 | Scherr . |
| 5,723,482 | 3/1998 | Degwert et al. . |
| 5,728,373 | 3/1998 | Alert et al. . |
| 5,759,520 | 6/1998 | Sachetto . |
| 5,760,111 | 6/1998 | Birbaum et al. . |
| 5,780,042 | 7/1998 | Gers-Barlag et al. . |

FOREIGN PATENT DOCUMENTS

| | | |
|---|---|---|
| 38 10 730 | 10/1989 | (DE) . |
| 0 414 920 A1 | 3/1991 | (EP) . |
| 998776 | 7/1965 | (GB) . |
| 1 123 868 | 8/1968 | (GB) . |
| 1 527 061 | 10/1978 | (GB) . |
| 44-12908 | 6/1969 | (JP) . |
| 9221415 | 5/1989 | (JP) . |
| 1-301618 | 10/1989 | (JP) . |

OTHER PUBLICATIONS

Patent Abstracts of JP 44 012908, Jun. 10, 1969.

\* cited by examiner

*Primary Examiner*—Raj Bawa
(74) *Attorney, Agent, or Firm*—Morgan & Finnegan, LLP

(57) ABSTRACT

Aerosol compositions are provided that enhance the therapeutic action of ointments by producing, upon topical application thereof, a sustained cooling effect that provides fast relief form pain and itching as well as a tendency to shrink swollen, inflamed tissue. The compositions contain oils, thickening agents for the oils, and propellant. Aqueous solutions, therapeutic ingredients and various adjuvants may also be present. The specific propellant and the proportion used are selected to provide a deposit with a temperature of about −5° C. to about +5° C. In this temperature range, the deposit is cold enough for the required therapeutic effect, but not so cold as to cause pain or tissue damage. The choice and proportion of thickening agents used are selected to provide a deposit that does not flow or spread. Were the deposit to spread, it would present a large surface area from which propellant present in the deposit would evaporate rapidly. By avoiding spreading, the propellant evaporates more slowly and the cooling effect is more sustained.

29 Claims, No Drawings

AEROSOL OINTMENT COMPOSITIONS FOR TOPICAL USE

This is a continuation-in-part of application Ser. No. 09/174,858, filed Oct. 19, 1998 now abandoned, which is a continuation-in-part of U.S. Ser. No. 09/075,067 filed May 8, 1998, now abandoned, which is a continuation-in-part of U.S. Ser. No. 08/947,530 filed Oct. 2, 1997, now abandoned.

BACKGROUND OF THE INVENTION

U.S. Pat. No. 4,422,887 to Spitzer et al discloses aerosol synthetic polymer—liquefied propellant compositions which when expelled from an aerosol container form cold pad polymeric foamed structures whose temperature is initially at least 30° C. below the ambient temperature at which the cold formed structure is formed, said formed structures containing open and/or closed cells which may contain an additive which is deposited in the pores and/or walls of the foamed structure as the foamed structure is formed. The aforedescribed prior art aerosol compositions when expelled on a surface exert a pronounced cooling effect on said surface until the propellant component thereof is completely evaporated.

The essential ingredients of the aerosol compositions of the above-mentioned U.S. Pat. No. 4,422,887 are:

a. a film-forming synthetic polymer in an amount within the range from about 2% to about 30% by weight of the composition;

b. at least one liquefied propellant boiling below –10° C.;

c. the total propellant being in an amount within the range from about 50% to about 90% by weight of the composition; and having a heat vaporization of at least 55 calories per gram; the propellant being capable of dissolving the synthetic polymer at least in the presence of a co-solvent that is soluble in the propellant and in solutions of the synthetic polymer in the propellant at ambient temperature; and d. at least one nonsolvent that is soluble in the propellant but in which the synthetic polymer is insoluble in an amount within the range from about 1% to about 85% by weight of the composition;

the composition forming on volatilization of propellant at ambient temperature a coherent formed structure containing open and/or closed cells, and having a temperature at least 30° C. below ambient temperature.

SUMMARY OF THE INVENTION

The present invention relates to an aerosol composition consisting essentially of the ingredients of an ointment-liquefied propellant composition which when expelled from an aerosol container onto damaged tissue provides a cold ointment which exerts a therapeutic effect on said tissue in contact therewith.

The cooling effect provided by the expelled composition of this invention is controlled so as to provide relief of pain for a desirable period of time but not too cold to cause discomfort or tissue damage.

Thus, an object of this invention is to provide a therapeutic ointment composition which when expelled from an aerosol container is cold enough to provide a cooling effect for pain relief but not too cold as to cause discomfort to damaged tissue to which the ointment is applied, said ointment also exerting a therapeutic effect on damaged tissue in contact therewith.

A further object is an ointment that can deliver appropriate medication as well as a cooling effect where it is applied.

Another object of the invention is to provide a cold ointment for the temporary relief of hemorrhoids which when applied to the swollen inflamed tissue provides a cooling effect and quickly relieving pain and itching as well as effecting shrinking of swollen inflamed tissue.

A still further object of the invention is an ointment for the treatment of sunburn.

Another object of the invention is a cold anti-itch ointment as well as one that provides relief from arthritic pain.

Another object of the invention is an antifungal ointment.

An object of this invention is an antibacterial ointment.

An additional object of the invention is to provide a cold ointment that is initially unctious, but dries to leave a deposit that is neither greasy nor oily.

More particularly, the present invention relates to novel aerosol compositions that enhance the therapeutic action of an ointment by instantly producing, upon topical application thereof, a sustained cooling effect which provides fast relief from pain and itching as well as a tendency to shrink swollen, inflamed tissue in advance of the slower action of any medication present in the ointment, said aerosol composition consisting essentially of from about 10 to about 60 percent by weight of ointment ingredients and from about 40 to about 90 percent by weight of liquefied propellant that is predominantly a non-polar propellant, i.e., at least about 80% by weight of the non-polar propellant and where the sum of the ointment ingredients and the propellant equals 100 percent by weight of the composition.

In another embodiment, applicants' invention is directed to a therapeutic aerosol composition for topical use consisting of (a) from about 10 to about 60 percent by weight of the ingredients of an ointment and (b) from about 40 to about 90 percent by weight of liquefied propellant, where at least about 80 percent by weight of the liquefied propellant is a non-polar propellant or mixture of non-polar propellants selected from the group consisting of a hydrocarbon propellant and a fluorocarbon propellant and the sum of ingredients from (a) and (b) equals 100 percent by weight of the composition, the composition when expelled from an aerosol device containing the composition depositing as an ointment having a solid or semi-solid consistency and a temperature between about –5° C. and +5° C.

Preferably, the ointment ingredients constitute from 35 to 100 percent by weight of an oil phase and from 0 to about 65 percent by weight of an aqueous phase based on the weight of the ointment ingredients and the oil phase of the ointment does not flow below about 35° C. The oil phase includes ingredients selected from the group consisting of oils, and oil soluble ingredients, the oil soluble ingredients including adjuvants, topical therapeutic agents, oil soluble emulsifiers, and thickening agents for the oils and oil soluble ingredients, where the oils and oil-soluble ingredients are soluble in the propellant. The aqueous phase includes water, water-soluble emulsifying agents and may also include topical therapeutic agents, humectants and alcohols.

Also, the present invention relates to a novel method for enhancing the therapeutic effect of a solid or semi-solid ointment which consists of dissolving and/or dispersing:

(a) from about 10 to about 60 percent by weight of an ointment that contains an oil phase and may contain an aqueous phase in the form of an emulsion, where the oil phase of the ointment does not flow below about 35° C., in (b) about 40 to about 90 percent by weight of a liquefied propellant that is at least 80 percent non-polar propellant in an aerosol container, whereby a solid or semisolid deposit is formed when a portion of the composition is expelled and this deposit placed in contact with injured tissue it provides instant relief from pain and itching as the result of its sustained cold, thereby enhancing the performance of the ointment with its slower action medications.

The compositions used in the practice of this invention consist essentially of an ointment, i.e., a solid or semisolid component, dissolved and/or dispersed in a liquefied propellant in a suitable aerosol container. The product is expelled from the aerosol container either as a deposit confined to a small area or as a spray covering a wider area, depending on the application. Thus, to relieve hemorrhoids the deposit should be confined to a small area, while to relieve sunburn a wider area is likely to be more convenient.

The expelled therapeutic composition for this invention will feel cold due to the evaporation of the propellant. A substantial portion of the propellant that is expelled should initially be part of the deposit, so that there is a continuing cooling action as the propellant gradually evaporates. It is also important that the deposit have a comparatively high density and that it be applied thickly.

The temperature of the expelled deposit should be initially in the range of about −5° C. to about +5° C. In this range the deposit can have the therapeutic effects that are the objects of this invention while not being so cold as to cause pain or tissue damage. Suitable liquefied nonpolar propellants that can be used in aerosol compositions of this invention to obtain a deposit falling within this temperature range include the hydrocarbon propellants, e.g., n-butane, isobutane and propane; the fluorocarbon propellants, e.g., 1,1-difluoroethane; and mixtures of these liquefied nonpolar propellants.

It has now been found that n-butane is the preferred propellant for use in the compositions of this invention. n-Butane has a vapor pressure of 17 p.s.i.g. and a boiling point of −0.5° C. and will tend to maintain the deposit at about that temperature. If the deposit gets much cooler, further cooling by evaporation will slow substantially. The deposit will remain in the required temperature range until the proportion of n-butane in the deposit has become quite low. If a significant amount of liquefied propellant remains with the deposit when it reaches the substrate, the temperature of the deposit will approximate the boiling point of the propellant. Once it reaches that temperature, the rate of evaporation will slow and absorption of heat from the substrate will prevent it from falling much lower. One reason for preferring n-butane is that a deposit containing it is not likely to become objectionally cold. In contrast, isobutane with a boiling point of −11.7° C. is likely to be unpleasantly cold, if the deposit contains a significant amount of liquefied isobutane.

A related reason for preferring n-butane is that it has a lower vapor pressure than the more widely used liquefied propellants: isobutane and propane. The lower vapor pressure assures that less propellant will be lost through evaporation as the exudate travels from the aerosol valve to the substrate upon which it is to be deposited.

However, for those products that are likely to be used at lower ambient temperatures, where n-butane does not provide sufficient pressure to expel the composition properly, it is advantageous to combine n-butane with a lesser amount of a higher vapor pressure propellant, e.g., isobutane, propane, 1,1-difluorethane or dimethyl ether.

However, higher vapor pressure (lower boiling point) propellants can be used under conditions when little if any liquefied propellant remains with the deposit when it reaches the substrate so that the temperature of the deposit is in the required range of −5° C. to +5° C. This can be done by reducing the percent propellant in the composition. A beneficial feature is that the higher the vapor pressure (lower the boiling point) of the propellant, the greater the tendency to flash off before reaching the substrate. Nonetheless, in general, the higher vapor pressure propellants are not as effective as n-butane, the preferred propellant.

The distance of the spray path as well as the characteristics of the package play a role in determining how much propellant will be lost as the exudate travels to the substrate upon which it will be deposited. It is evident that the longer the spray path, the more propellant will be lost by evaporation before reaching the substrate and the less propellant will be available for sustained cooling. It has also been found that restrictions in the delivery system also promote early evaporation of propellant by reducing the flow rate of the exudate.

However, with some compositions a restricted delivery system is beneficial, since it results in a heavier-bodied deposit. Also, where layering of the composition occurs within the container, it is advantageous to employ a capillary dip tube, i.e., a dip tube with an inside diameter of 1 mm., to minimize the amount of separated material that is released after first shaking the container. Shaking is not effective in mixing material that is in the dip tube.

The dynamic physical characteristics of the composition play an important role in determining the amount of propellant in the deposit and the amount of time it will remain in the deposit to provide sustained cooling. The aerosol compositions of this invention consist of the ingredients of an ointment that generally contains a thickening agent in a solution of an oil, and often one or more medicinal ingredients, dispersed and/or dissolved in an appropriate propellant so that the expelled deposit is initially in the range of about −5° C. to about +5° C. As product is expelled there is some loss of propellant accompanied by cooling of the exudate. If the deposit had been a liquid rather than an ointment, it would have spread rapidly whereby expiration of the propellant would occur too quickly and one would not obtain the desired sustained cooling effect. The compositions of this invention deposit as solids or semi-solids. The thickness of the deposit helps to provide sustained therapeutic cooling.

It has been found that the oil phase of the ointment should have a flow temperature that is at least about 35° C.; otherwise, the deposit will liquefy readily and not provide sufficient cooling. It is advantageous that the flow temperature of the oil phase of the ointment not exceed about 60° C., otherwise manufacture becomes more difficult.

The preferred compositions contained in an appropriate aerosol container in accordance with this invention contain from about 10 to about 60 percent by weight of the ingredients of an ointment and from about 40 to about 90 percent by weight of a propellant that is at least 80% by weight n-butane. Also preferred are aerosol compositions of this invention that consist essentially of from about 50% to about 75% by weight of a non-polar propellant or mixture of non-polar propellants and 25% to 50% by weight of ingredients of an ointment.

DETAILED DESCRIPTION OF THE INVENTION

The ointment ingredients of the composition contained in an aerosol container in accordance with the present invention includes such medically active ingredients, petroleum jellies, oils, volatile liquids, thickening agents, surfactants, and dispersed solids as may be present in the composition. Adjuvants such as known fragrances, corrosion inhibitors, preservatives, and coloring agents may also be present as ointment ingredients.

Oils that may be used in the compositions include mineral oils, silicone oils, vegetable oils such as corn oil, safflower oil, soya oil, cod liver oil, and shark liver oil and synthetic oils such as isopropyl myristate, butyl stearate and dimethyl sebacate.

Volatile organic liquids boiling below about 250° C. may be used as partial or complete replacements of the oils, to provide an ointment component that dries to leave a non-greasy, non-oily residue. The polydimethylcyclosiloxanes having 3 to 5 silicone atoms are particularly useful, because of their low potential to cause irritation.

Thickening agents that may be used include mineral waxes such as paraffin and microcrystalline waxes, animal and vegetable waxes such as beeswax, wool wax, spermaceti and bayberry wax, synthetic waxes such as hydrogenated caster oil, glyceryl monostearate, cetyl palmitate and cetyl alcohol; polymers such as polyethylene and polyisobutylene and metallic soaps such as aluminum distearate. The thickening agent(s) for oils and oil soluble ingredients present in the ointment is/(are) present in the aerosol composition of this invention in a sufficient amount such that the composition when expelled from an aerosol device, deposits as a solid or semi-solid ointment. The aerosol composition of this invention may contain between 10% and 60% by weight of thickening agent(s) based on the weight of the oil phase, as part of the oil-phase ingredients of the ointment.

Water may also be included in the ointment component in the form of a water-in-oil emulsion. Water is useful in a number of ways. It can act as a solvent or a dispersion medium for an active imgredient. It evaporates so that less residue remains on the skin. It reduces costs by replacing more expensive ingredients. When a portion of the aerosol composition is expelled, the deposit is a cold ointment-like structure that is a water-in-oil emulsion.

When water is included in the composition, emulsifying agents are also added to facilitate the formation of a water-in-oil emulsion. Generally, a water-soluble and an oil-soluble emulsifier are used in combination. Oil-soluble emulsifiers include the di- and tri-ethanoxy esters of lauric, myristic, palmitic and stearic acids, and the di and tri-ethanoxy ethers of lauryl alcohol, cetyl alcohol, oleyl alcohol and lanolin alcohols. Glyceryl monostearate also serves as an oil-soluble emulsifier.

Water-soluble emulsifiers include the decylethanoxy esters and ethers of the above acids and alcohols, respectively; water-soluble soaps, such as potassium palmitate; anionic surfactants, such as sodium lauryl sulfate, sodium lauroyl sarcosinate and sodium stearoyl lactate; amphoteric surfactants, such as the sodium salts of the imidazoline monocarboxyl stearyl derivative and the imidazoline dicarboxyl coconut derivative; and cationic surfactants, such a cetyltrimethylammonium bromide.

When water, along with water-soluble emulifiers, are used in the compositions, it is necessary that they be used judiciously so that an aqueous foam is not formed when product is released from the container. An aqueous foam will neither produce nor sustain the required temperature when n-butane is used as the propellant. Including the water in the ointment in the form of a water-in-oil emulsion assures that an aqueous foam will not form.

Under certain conditions, the ointment ingredients used in the preparation of the aerosol composition can be an oil-in-water emulsion. The necessary condition is that the combination of hydrophilic and hydrophobic emulsifiers be balanced so that the type of emulsion, whether water-in-oil or oil-in-water, will depend on the volume ratio of the oil phase and the water phase. Thus, adding water to the water-in-oil emulsion will convert it to an oil-in-water emulsion. Alternatively, adding a hydrophobic liquid to an oil-in-water emulsion will convert it to a water-in-oil emulsion.

In the instant invention, ointment ingredients that produce an oil-in-water emulsion are combined with a hydrophobic or non-polar propellant, i.e., n-butane, to form a water-in-oil emulsion. This emulsion may be unstable, due to the dilution effect of the relatively large volume of propellant on the emulsifiers. When a portion of the composition is expelled from the aerosol containers, the propellant component starts to evaporate. Initially, the deposit on the skin should contain sufficient propellant that it is a solid or semi-solid water-in-oil emulsion. As the deposit is rubbed into the skin, the remainder of the propellant evaporates, causing the residue to revert back to an oil-in-water emulsion that can be rinsed off with water.

Thus, the conditions necessary for the use of ointment ingredients that make an oil-in-water emulsion are: (a) the emulsifier system should be balanced so that the type of emulsion that forms depends on the volume ratio of oil and water phases, (b) sufficient liquefied propellant should be present in the deposit initially so that the deposit is a solid or semi-solid water-in-oil emulsion, and (c) the oil phase of the ointment ingredients of the composition should be non-flowable below about 35° C.

When water is included in the composition, it is sometimes beneficial to include ethyl alcohol or isopropyl alcohol. Humectants, such as propylene glycol, glycerine or sorbitol may also be used. Preservatives, such as sorbic acid, methyl paraben and propyl paraben may be included. Also, corrosion inhibitors, such as sodium benzoate, may be used.

Various therapeutic agents may also be included in the composition. These include local anesthetic ingredients such as benzocaine, dibucaine, lidocaine and pramoxine hydrochloride; antipruritic agents such as menthol and camphor; vasoconstrictors such as ephedrine sulfate, epinephrine and phenylephrine hydrochloride; antiseptics such as hexyl resorcinol, bithionol and triclocarban; antibiotics such as bacitracin, polymyxin, mystatin and neomycin; anti-inflammatory agents such as hydrocortisone; counter-irritants such as methyl salicylate; rubefacients such as methyl nicotinate; and antifungal agents such as miconazole and ketoconazole nitrates. Preferably, therapeutic agents are included in the aerosol composition in an therapeutically effective amount.

For the preparation of the compositions of this invention, ointments are prepared in the conventional manner. Generally, the ingredients are combined and heated with stirring until all ingredients have dissolved, except for those ingredients that are not soluble or are heat sensitive. These are added after the ointment has cooled sufficiently. The ointment is stirred while cooling. It is dosed into the aerosol containers at a temperature above its flow temperature.

When an aqueous phase is part of the ointment composition, ingredients that are soluble or dispersible in that phase are combined with it. Preferably, the aqueous phase is then blended with the non-aqueous phase at a temperature above the flow temperature of the non-aqueous phase to form an emulsion. The two phases, either separately or as a preformed emulsion, are dosed into the aerosol containers at a temperature above their flow temperatures.

Vacuum is applied to the containers to remove air and the propellant is added either before or after clinching of the valves. Either before or after adding the actuators and cover caps, the packages are passed through a water bath that is warm enough to raise the temperature of the composition above the flow temperature of the oil phase of the ointment component. Shaking causes the ointment to blend with the propellant.

The studies that resulted in this invention were conducted using compositions packaged in aerosol containers fitted with valves with one or two 0.5 mm. diameter orifices and 1 mm. inside diameter dip tubes. The actuator had a spout with a 1 mm. diameter opening. From 2.5 to 5.0 grams of composition were expelled onto a paper held 2.5 cm. from the spout. The temperature was measured starting within 30 seconds from the time the material was expelled, and the minimum temperature of the deposit was determined using an electronic thermometer with the probe inserted in the deposit with the paper folded so that as much of the deposit as possible surrounded the temperature probe. These test conditions were used in establishing the preferred temperature range and in determining how long the temperature was sustained.

To study various physical effects, actuators, valves and dip tubes with different size openings were used. Tests were also conducted when the distance between the actuator and the paper substrate were varied.

The following Examples 1–15 illustrate preferred embodiments of the invention:

EXAMPLE 1

Aerosol Ointment Composition For Treatment Of Hemorrhoids

|  | Parts By Weight |
| --- | --- |
| Petroleum jelly (1) | 26.4 |
| Microcrystalline wax (2) | 6.6 |
| Epinephrine | 0.01 |
| Pramoxine hydrochloride | 1.0 |
| n-Butane | 66.0 |

(1) flow temperature = 41° C.
(2) melting point = 74° C.
Ointment flow temperature = 48° C.

This example illustrates an aerosol composition for the relief of hemorrhoids. It was prepared by first milling the pramoxine hydrochloride with the petroleum jelly until the dispersion was complete. The dispersion was then combined with the wax and heated with stirring until the wax had dissolved in the petroleum jelly. The composition was then cooled to 55° C. and the epinephrine mixed in. The fluid solution was added to the aerosol cans, valves were clinched on, vacuum was applied to remove air in the cans and n-butane was added under pressure. The filled cans were placed in a heated water bath to check for leaks and to bring the composition to a temperature above the flow temperature of the ointment. Spout actuators with a 1 mm. opening were placed on the valves and the cans were shaken to dissolve and/or disperse the ointment in the n-butane.

To use, the container was shaken and then held with the actuator close to a double layer of toilet tissue. About a 2 gram deposit was expelled onto the tissue. The ointment on the tissue was held against the hemorrhoids until it no longer felt cold. The sustained cold had the immediate effect of providing relief from burning and itching, while simultaneously the inflamed tissue appeared to shrink and recede to its normal position. These immediate beneficial effects due to the sustained cold were continued by the actions of the local anaesthetic and the vasoconstrictor present in the ointment.

EXAMPLE 2

Aerosol Ointment Composition For Treatment Of Sunburn

|  | Parts By Weight |
| --- | --- |
| Glyceryl monostearate (1) | 11.6 |
| Isopropyl myristate | 17.4 |
| Camphor | 1.0 |
| n-Butane | 70.0 |

(1) melting points = 57.5° C.
Ointment flow temperature = 44° C.

Example 2 illustrates an ointment composition for treatment of sunburn. It was prepared by heating with stirring to dissolve the glyceryl monostearate and camphor in the isopropyl myristate. The solution was cooled to 50° C. and dosed into aerosol cans. Valves were crimped onto the cans, a vacuum was drawn and the propellant was added under pressure. The filled cans were placed in a heated water bath to check for leaks and to bring the composition above the flow temperature of the ointment. The cans were then shaken. The molten ointment mixes readily with the propellant in which it is dissolved and/or dispersed. Spray actuators with a 0.5 mm. diameter opening were fitted on the valves.

To use, the container was shaken and held only a few cm. from the sunburned area before spraying. The sustained cold quickly relieved burning and itching sensations due to the sunburn. The ointment was then spread to more uniformly cover the sunburned area. The antipruritic agent present in the composition continues the therapeutic effect.

EXAMPLE 3

Aerosol Ointment Composition For Treatment Of Arthritic Pain

|  | Parts By Weight |
| --- | --- |
| Glyceryl monostearate (1) | 17 |
| Methyl salicylate | 17 |
| n-Butane | 66 |

(1) melting point = 57.5° C.
Ointment flow temperature = 38° C.

This example illustrates an aerosol composition for the relief of arthritic pain. The glyceryl monostearate and methyl salicylate were combined and heated to dissolve the glyceryl monostearate. The remainder of the procedure was the same as example 2, except that spout actuators with a 1 mm. diameter opening were used instead of spray actuators.

To use, the aerosol can was shaken and a small amount of the cold ointment was expelled and spread over the arthritic area. The sustained cold provided quick relief. The ointment was then rubbed into the area. As it was being rubbed in, the warm counter-irritant action of the methyl salicylate could be felt through the cold.

EXAMPLE 4

Aerosol Ointment Composition For Treatment For Relieving Itching

|  | Parts By Weight |
|---|---|
| Glyceryl monostearate (1) | 10 |
| 2 Hexyldecanol | 15 |
| Hydrocortisone | 1 |
| n-Butane | 64 |
| Isobutane | 10 |

(1) melting point = 57.5° C.
Ointment flow temperature = 40° C.

The hydrocortisone aerosol composition provides instant relief from itching. The glyceryl monostearate, 2-hexyldecanol and hydrocortisone were combined and heated with stirring to obtain a clear solution. The remainder of the procedure was the same as in example 2, except that spout actuators with a 1 mm. opening were used. When the aerosol ointment was applied, itching quickly stopped due to the sustained cold. The antipruritic effect continued throughout the day, presumable due to the action of the hydrocortisone.

EXAMPLE 5

Aerosol Ointment Composition For The Relief Of Itching

|  | Parts By Weight |
|---|---|
| Glyceryl monostearate (1) | 5.0 |
| Dimethylcyclopolysiloxane (2) | 12.0 |
| Hydrocortisone | 1.0 |
| Disodium cocoamphodipropionate | 0.2 |
| Water | 15.8 |
| n-Butane | 66.0 |

(1) melting point = 57.5° C.
(2) DC 245 Fluid (Dow Corning Corp.)
Ointment flow temperature = 45° C.

Example 5 illustrates a hydrocortisone ointment composition for the relief of itching, where the ointment component is a water-in-oil emulsion. It was prepared by combining the oil-soluble components, heating to dissolve the glyceryl monostearate, and then cooling with mixing until it started to thicken. The water-soluble surfactant was dissolved in the water and heated to the temperature of the oil mixture. The aqueous solution was mixed into the oil phase to form a water-in-oil emulsion, which was heated until it flowed, and then dosed into aerosol cans. The remainder of the procedure was the same as in Example 1.

EXAMPLE 6

Aerosol Ointment Composition For The Relief of Muscle Aches

|  | Parts By Weight |
|---|---|
| Glyceryl monostearate (1) | 8.6 |
| Dimethylcyclopolysiloxane (2) | 6.5 |
| Mineral oil | 6.5 |
| Menthol | 2.0 |
| Disodium cocoamphodipropionate | 0.15 |

-continued

|  | Parts By Weight |
|---|---|
| Water | 9.8 |
| n-Butane | 66.45 |

(1) melting point = 57.5° C.
(2) DC 245 Fluid (Dow Corning Corp.)
Ointment flow temperature = 41° C.

Example 6 illustrates an ointment composition for the relief of muscle aches, where the ointment component is a water-in-oil emulsion. The procedure is the same as in Example 5.

The benefit derived from using compositions based on water-in-oil emulsions, especially when part of the oil phase is volatile, is that when applied topically the residue is not greasy or oily.

EXAMPLES 7 AND 8

Aerosols Composition Containing Ointments That Are Oil In Water Emulsions

|  | Parts By Weight | |
|---|---|---|
|  | 7 | 8 |
| Part A | | |
| Glyceryl monostearate (1) | 4.2 | 4.2 |
| Cetyl alcohol (2) | 1.0 | 1.0 |
| Mineral oil | 11.5 | 11.5 |
| Part B | | |
| Mackam 2CSF-70 (3) | 1.0 | — |
| Pluronic F68 (4) | — | 1.0 |
| Water | 15.6 | 15.6 |
| Part C | | |
| n-Butane | 66.7 | 66.7 |

(1) melting point = 57.5° C.
(2) melting point = 45–50° C.
(3) 70% disodium cocoamphodipropionate in propylene glycol
(4) polyoxyethylene-polyoxypropylene
flow temperature of part A = 39–40° C.

Before preparing each example, the water phase (part B) was added in increments to 10 g. of the oil phase (Part A), stirring and heating as required to maintain the molten oil phase as a liquid. It was found for example 7 that 10 g. of the water phase was required to convert the water-in-oil emulsion that formed initially to an oil-in-water emulsion. For example 8, the formation of a water-in-oil emulsion followed by its conversion to an oil-in-water emulsion required 7 g.

In the same manner, each example was prepared by adding part B to part A in increments with stirring, heating as required. The propellant was added through the valve. The can was then placed in a water bath at 50° C. and kept there for a sufficient period to bring the contents of the can to 45° C. Then, it was removed form the water bath and shaken. The valve stem was fitted with an actuator.

Subsequently, examples 7 and 8 were evaluated. Both examples gave cold semi-solid deposits of an ointment-like consistency when small amounts were applied to the skin. There was no evidence of aqueous foam formation with either example, as would have been the case if they had been expelled as oil-in-water emulsions. They spread smoothly on the skin, and could be rinsed off with water.

EXAMPLES 9 AND 10

Aerosol Ointment Compositions Containing Antifungal And Antibacterial Agents, Respectively

|  | Parts By Weight | |
| --- | --- | --- |
|  | Example 9 Antifungal | Example 10 Antibacterial |
| Part A | | |
| Glyceryl monostearate (1) | 2.8 | 3.9 |
| Cetyl alcohol (2) | 0.9 | 1.3 |
| Menthol | 0.3 | 0.4 |
| Dimethyl cyclosiloxane | 3.0 | 4.2 |
| Isopropyl myristate | 1.7 | 3.4 |
| Mineral oil | 1.1 | 3.3 |
| Petroleum jelly | 1.3 | |
| Methyl paraben | 0.07 | 0.07 |
| Propyl paraben | 0.03 | 0.03 |
| Part B | | |
| Polysorbate 20 | 0.33 | 0.5 |
| Polysorbate 40 | 0.33 | |
| Neomycin | | 0.17 |
| Water | 20.6 | 16.0 |
| Part C | | |
| Micronazole nitrate | 0.67 | |
| Magnesium stearate | 0.2 | |
| Part D | | |
| n-Butane | 66.6 | 66.7 |

(1) melting point = 57.5° C.;
(2) melting point = 45–50° C.;
(3) DC 345 Fluid
Flow temperature of Part A = 42° C.

Preparation

Parts A and B are separately prepared by combining ingredients and heating with stirring to dissolve. Both parts are heated to 50–55° C. and part B is slowly added to part A with stirring to form an emulsion. Without cooling, part C is mixed in and homogenized. With the emulsion at 45–50° C., the emulsion is dosed into aerosol cans. Valves are clinched on the cans and part D is added. The cans are placed in a heated water bath to bring the contents in the cans to 45° C. or higher. The cans are shaken well on a vibrator or a case shaker. The aerosol ointment preparation of Examples 9 and 10, respectively, when expelled from an aerosol can, provides a cold semi-solid or solid deposit initially between about −5° C. and +5° C.

EXAMPLE 11

Aerosol Composition Useful For The Relief Of Sunburn

The aerosol composition is prepared as in example 8, except that 0.3 parts by weight of water are replaced with 0.3 parts by weight of pramoxine hydrochloride. The aerosol ointment preparation of Example 11 when expelled from an aerosol can, provides a cold semi-solid or solid deposit initially between about −5° C. and +5° C.

EXAMPLE 12

Aerosol Composition Useful As A Topical Antiseptic.

The aerosol composition is prepared as in example 7, except that 0.3 parts by weight of mineral oil are replaced by 0.3 parts by weight of bithional. The aerosol ointment preparation of Example 12 when expelled from an aerosol can, provides a cold semi-solid or solid deposit initially between about 5° C. and +5° C.

EXAMPLE 13

Aerosol Composition Useful As An Antipruritic

The aerosol composition is prepared as in example 10, except that 0.17 parts by weight of neomycin and 0.17 parts by weight of water are replaced by 0.34 parts by weight of pramoxine hydrochloride. The aerosol ointment preparation of Example 13 when expelled from an aerosol can, provides a cold semi-solid or solid deposit initially between about 5° C. and +5° C.

EXAMPLES 14 AND 15

Aerosol Compositions Useful For Relief of Hemorrhoids

The following examples 14 and 15 illustrate the use of isobutane and a mixture of propellants that includes propane for the preparation of aerosol compositions that may be used for the relief of hemorrhoids. Propane has too high a vapor pressure to be used alone in retail aerosol products. Instead, it is commonly used in combination with isobutane, which has a lower vapor pressure. The vehicles used in these examples may also be used for other product applications, often by simply changing the active ingredient or by adding an additional active ingredient. For instance, by replacing 0.5 parts by weight of water with menthol in the preparation, Example 14 illustrates an aerosol composition preparation that, when expelled from an aerosol can, provides a solid or semi-solid ointment that is effective as an antipruritic. Example 14 may be used to prepare an aerosol composition preparation that, when expelled from an aerosol can, is effective for the relief of sunburn, by replacing 0.5 parts of water with cetyl pyridinium chloride in the preparation.

|  | Parts by Weight | |
| --- | --- | --- |
|  | Example 14 | Example 15 |
| Part A | | |
| Glyceryl monostearate (1) | 3.6 | 9.2 |
| Cetyl alcohol (2) | 1.8 | 4.6 |
| Isopropyl myristate | 3.6 | 9.2 |
| Mineral oil | 9.0 | 23.0 |
| Part B | | |
| Polysorbate 20 | 0.8 | — |
| Pramoxine hydrochloride | 0.5 | — |
| Water | 25.7 | — |
| Part C | | |
| Isobutane | 55.0 | — |
| A 46 (3) | — | 54.0 |

(1) melting point = 57.5° C.;
(2) melting point = 45–50° C.
(3) mixture of propane and isobutane with a vapor pressure of 46 p.s.i.g.
Flow temperature of part A is 43° C.

Preparation

Parts A and B are prepared separately by combining ingredients and heating with stirring to dissolve the ingredients in oil or water, respectively. Both parts A and B are brought to a temperature of 50–55° C. and part B is slowly added to part A with stirring to form an emulsion. With the emulsion at a temperature of 45–50° C., the emulsion is dosed into aerosol cans. Valves are clinched on the aerosol can and part C is added to the aerosol cans. The cans are placed in a heated water bath to bring the contents in the aerosol cans to a temperature of 45° C., or higher. The cans are shaken well on a vibrator or case shaker. The aerosol composition preparations of Examples 14 and 15, when expelled from an aerosol can, provide a cold solid or semi-solid deposit initially between about −5° C. and +5° C.

Changes in construction will occur to those skilled in the art and various apparently different modifications and embodiments may be made without departing from the scope of the invention. The matter set forth in the foregoing description is offered by way of illustration only. The actual scope of the invention is intended to be defined in the following claims when viewed in their proper perspective against the prior art.

We claim:

1. A therapeutic aerosol composition for topical use consisting of:

(a) from about 10 to about 60 percent by weight of the following ingredients:

oils selected from the group consisting of mineral oils, vegetable oils, silicone oils and synthetic oils;

thickening agents for the oils in an amount sufficient to thicken the oils to a non-flowable state below about 35° C., said thickening agents being selected from the group consisting of mineral waxes, animal and vegetable waxes, synthetic waxes, polymers and metallic soaps; and optionally ingredients selected from the group consisting of an aqueous solution, adjuvants, topical therapeutic agents and emulsifiers, and (b) from about 40 to about 90 percent by weight of liquefied propellant, where at least about 80 percent by weight of the liquefied propellant is a non-polar propellant or mixture of non-polar propellants selected from the group consisting of hydrocarbon and fluorocarbon propellants, and the sum of (a) and (b) equals 100 percent by weight of the composition, the composition when expelled from an aerosol device depositing as an ointment having a solid or semi-solid consistency containing a substantial proportion of said propellant, whose evaporation is restrained by the solid or semi-solid nature of the deposit, thereby upon topical application producing a sustained cooling effect at a temperature between about −5° C. and +5° C.

2. The aerosol composition according to claim 1, where the ingredients of (a) constitute from 35 to 100 percent by weight of an oil phase and from 0 to about 65 percent by weight of an aqueous solution based on the weight of the ingredients of (a).

3. The aerosol composition according to claim 2, where the ingredients of (a) include ingredients selected from the group consisting of, topical therapeutic agents and emulsifiers.

4. The aerosol composition according to claim 3, where the aqueous solution in (a) includes water, water-soluble emulsifying agents, and may also include said topical-therapeutic agents, humectants, and alcohol; and the aqueous solution when combined with the oils and thickening agents of (a) forms an emulsion that may be water-in-oil or oil-in-water.

5. The aerosol composition according to claim 1, where the liquefied propellant is n-butane.

6. The aerosol composition according to claim 1, where at least about 80 percent of the liquefied propellant is n-butane.

7. The aerosol composition according to claim 1, where the liquefied propellant is isobutane.

8. The aerosol composition according to claim 1, wherein the ingredients of (a) include a therapeutic agent that provides relief form the pain, itching and discomfort of hemorrhoids.

9. The aerosol composition according to claim 1, wherein the ingredients of (a) include a therapeutic agent that provides relief from the pain and discomfort of arthritis.

10. The aerosol composition according to claim 1, wherein the ingredients of (a) include a therapeutic agent that provides relief from itching.

11. The aerosol composition according to claim 1, wherein the ingredients of (a) include a therapeutic agent that provides relief from the burning and discomfort of sunburn.

12. The aerosol composition according to claim 1, wherein the ingredients of (a) include a therapeutic agent that provides relief form the pain and discomfort of muscle aches and strains.

13. The aerosol composition according to claim 3, containing glyceryl monostearate as a thickening agent.

14. The aerosol composition according to claim 1, that contains a corticosteroid as the therapeutic agent.

15. The aerosol composition according to claim 1, that contains a local anesthetic as the therapeutic agent.

16. The aerosol composition according to claim 1, that contains an analgesic as the therapeutic agent.

17. The aerosol composition according to claim 1, that contains a counter-irritant as the therapeutic agent.

18. The aerosol composition according to claim 1, that contains a vasoconstrictor as the therapeutic agent.

19. The aerosol composition according to claim 1, that contains methyl salicylate as the therapeutic agent.

20. The aerosol composition according to claim 1, that contains menthol as the therapeutic agent.

21. The aerosol composition according to claim 1, that contains an antifungal agent as the therapeutic agent.

22. The aerosol composition according to claim 1, that contains an antibacterial agent as the therapeutic agent.

23. The aerosol composition according to claim 1, where the ingredients of (a) include a volatile silicone fluid boiling below about 250° C.

24. The aerosol composition according to claim 4, where the emulsion component is a water-in-oil emulsion.

25. The aerosol composition according to claim 1 when delivered in the form of an aerosol from the aerosol can deposits cold solid or semi-solid ointment that is a water-in-oil emulsion.

26. The aerosol composition according to claim 4, where the emulsion is a oil-in-water emulsion.

27. The aerosol composition according to claim 4, where the emulsifiers are hydrophilic and hydrophobic and are balanced so that the emulsion, whether water-in-oil or oil-in-water, depends on the volume ratio of the oil and water solutions.

28. The composition according to claim 1, wherein (b) includes about 50 to about 90 percent by weight of liquefied propellant.

29. The composition according to claim 28, wherein (b) includes about 50 to about 75 percent by weight of liquefied propellant.

* * * * *